(12) United States Patent
Papenmeier et al.

(10) Patent No.: US 10,132,788 B2
(45) Date of Patent: Nov. 20, 2018

(54) METHODS OF SEPARATION OF A METAL FROM ITS LIQUID-SOLUBLE OXIDE FOR ANALYSIS

(71) Applicant: The United States of America as represented by the Secretary of the Navy, Washington, DC (US)

(72) Inventors: Douglas M. Papenmeier, Bloomington, IN (US); Steven M. Lovejoy, Sebastopol, CA (US); Henry Ye, San Mateo, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 17 days.

(21) Appl. No.: 15/261,769

(22) Filed: Sep. 9, 2016

(65) Prior Publication Data
US 2017/0138920 A1 May 18, 2017

Related U.S. Application Data

(60) Provisional application No. 62/236,216, filed on Oct. 2, 2015.

(51) Int. Cl.
| | |
|---|---|
| *G01N 33/20* | (2006.01) |
| *G01N 1/38* | (2006.01) |
| *G01N 1/40* | (2006.01) |
| *G01N 33/22* | (2006.01) |
| *G01N 21/73* | (2006.01) |
| *G01N 33/00* | (2006.01) |
| *G01N 1/00* | (2006.01) |

(52) U.S. Cl.
CPC ............. *G01N 33/20* (2013.01); *G01N 1/38* (2013.01); *G01N 1/4077* (2013.01); *G01N 21/73* (2013.01); *G01N 33/227* (2013.01); *G01N 2001/4088* (2013.01)

(58) Field of Classification Search
CPC .......... G01N 33/20; G01N 33/00; G01N 1/38; G01N 1/28; G01N 1/00
USPC ....................................................... 436/73
See application file for complete search history.

(56) References Cited

PUBLICATIONS

Galler et al, Boron speciation in acid digests of metallurgical grade silicon reveals problem for accurate boron quantification by inductively coupled plasma—optical emission spectroscopy, J. Anal. At. Spectrom, 2014, 29, 614-622. (Year: 2014).*
Papenmeier, Determining Boron Speciation with an Inductively Coupled Plasma Optical Emission Spectrometer, Propellants Explos. Pyrotech., 2015, 40, 927-930. (Year: 2015).*

* cited by examiner

*Primary Examiner* — Christine T Mui
(74) *Attorney, Agent, or Firm* — Christopher A. Monsey

(57) ABSTRACT

Various methods for separating a metal from its metal oxide for analysis are provided. For example, exemplary methods include approaches for providing a process for separating a metal from its water-soluble metal oxide in a pyrotechnic composition. Exemplary embodiments include a method of separation that allows for analysis of both metal and metal oxide using an elemental analysis technique, (e.g., inductively coupled plasma optical emission spectrometry (ICP-OES)) and determination of the relative amount of elemental metal and its oxide known as speciation.

12 Claims, 5 Drawing Sheets

30

| SAMPLE | RESIDUE | | | | | |
|---|---|---|---|---|---|---|
| | MASS (mg) | INTENSITY | [B] (mg/L) | STAND DEV | Wt% | ADJUSTED Wt% |
| BLANK | | 82190 | 0.056 | 0.010 | | |
| 1 | 29.0 | 1681213 | 1.309 | 0.0271 | 22.56 | 21.60 |
| 2 | 29.5 | 1710331 | 1.331 | 0.0092 | 22.56 | 21.61 |
| 3 | 28.9 | 1612405 | 1.255 | 0.0311 | 21.71 | 20.74 |
| AVERAGE | | | | | 22.30 | 21.32 |
| STND DEV | | | | | 0.50 | 0.498 |
| RSD | | | | | 2.20 | 2.34 |

| SAMPLE | SOLUBLE | | | | | |
| --- | --- | --- | --- | --- | --- | --- |
| | MASS (mg) | INTENSITY | [B] (mg/L) | STAND DEV | Wt% | ADJUSTED Wt% |
| BLANK | | 42059 | 0.025 | 0.0030 | | |
| 1 | 29.0 | 4403599 | 3.440 | 0.0028 | 0.297 | 0.2944 |
| 2 | 29.5 | 4708012 | 3.678 | 0.1119 | 0.312 | 0.3096 |
| 3 | 28.9 | 4075970 | 3.184 | 0.0579 | 0.275 | 0.2732 |
| AVERAGE | | | | | 0.295 | 0.2924 |
| STND DEV | | | | | 0.019 | 0.0182 |
| RSD | | | | | 6.316 | 6.236 |

FIG. 5

METHODS OF SEPARATION OF A METAL FROM ITS LIQUID-SOLUBLE OXIDE FOR ANALYSIS

CROSS-REFERENCE TO RELATED APPLICATIONS

The present application claims priority to U.S. Provisional Patent Application Ser. No. 62/236,216, filed Oct. 2, 2015, entitled "METHOD OF SEPARATION OF A METAL FROM ITS WATER-SOLUBLE OXIDE FOR ANALYSIS," the disclosure of which is expressly incorporated by reference herein.

STATEMENT REGARDING FEDERALLY SPONSORED RESEARCH OR DEVELOPMENT

The invention described herein includes contributions by one or more employees of the Department of the Navy made in performance of official duties and may be manufactured, used and licensed by or for the United States Government for any governmental purpose without payment of any royalties thereon. This invention (Navy Case 200,290) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND AND SUMMARY OF THE INVENTION

The present invention relates to methods for separating a metal from its metal oxide for analysis. The methods disclosed herein include approaches for providing a novel process for separating a metal from its water-soluble metal oxide in a pyrotechnic composition. Exemplary embodiments include a method of separation that allows for analysis of both metal and metal oxide using an elemental analysis technique, e.g., inductively coupled plasma optical emission spectrometry (ICP-OES) and determination of the relative amount of elemental metal and its oxide known as speciation.

Elemental boron is a commonly used pyrotechnic fuel with uses ranging from fireworks and airbags to defense and space exploration. However, boron is subject to oxidation by acids. The present invention is a method for distinguishing between elemental boron and the oxidized form $H_3BO_3$ $(B(OH)_3)$, developed to assess boron potassium nitrate $(BKNO_3)$, which is a widely-used initiator.

Generally, pyrotechnic compositions comprise a powdered metal and an oxidizer in intimate contact. An example of such a composition is boron potassium nitrate $(BKNO_3)$ where boron (B) is the fuel and nitrate $(NO_3^-)$ in potassium nitrate $(KNO_3)$ is the oxidizer. If too much of the metal becomes oxidized, the pyrotechnic will not function as designed, nor will the device into which the pyrotechnic composition has been inserted function as designed. Exemplary devices using this exemplary pyrotechnic mixture include gas generators which are small ordnance devices within a reserve battery or on larger missiles, airbag actuators in automobiles, and squibs designed to perform various functions on systems, such as on a vehicle airbag system, or on a missile or a rocket. Because many of these devices are expected to sit for years before functioning properly, assessment of the speciation, (e.g., the relative amount of metal and metal oxide), is a critical measure for determining how long and under what conditions the devices can be expected to function reliably. The present invention solves the problem of obtaining an accurate, efficient, and commercially viable speciation via the methods described herein.

According to an illustrative embodiment of the present disclosure, an exemplary method first weighs a sample in digestion vials, adding water to dissolve the metal oxide out of the sample for a specific period of time at a specific temperature filtering the sample, and bringing the filtrate containing borate, potassium, and nitrate ions, (e.g., $BKNO_3$), to a predetermined volume with an appropriate diluent. The filtration separates the water soluble oxide, (e.g., borate), from an elemental fuel, (e.g., boron). The residue is then digested by means of an appropriate digestant for a predetermined time at a predetermined temperature. The digested residue is then brought to a known volume with the same diluent material as was used with the filtrate. Next, both samples are ready for elemental analysis using a desired analytical technique used for detection of trace metals, (e.g., ICP-OES). A weight percent of both the elemental metal and the water-soluble oxide of that metal may then be computed using initial mass, and measured concentration of substances in both samples, (e.g., filtrate), digested water soluble oxide, and volume of each sample.

According to another illustrative embodiment of the present disclosure, the methods disclosed herein allow simultaneous analysis of metal and water-soluble metal oxide. According to a further illustrative embodiment of the present disclosure, exemplary methods disclosed herein may be used for assessment of shelf life of airbag actuators, namely the assessment of metal fuels other than boron with water-soluble oxides.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 4 shows exemplary calculation results for boron measurements of an exemplary residue portion; and FIG. 5 shows exemplary calculation results for boron measurements of an exemplary soluble portion.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1:
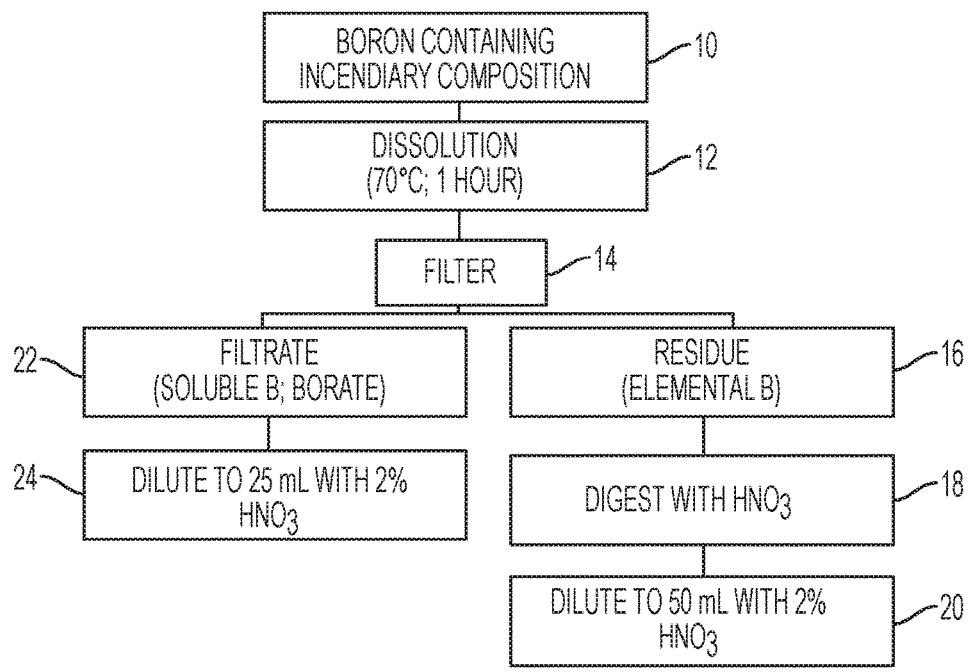
FIG. 1 shows a flow diagram illustrating an exemplary method of separating a metal from its water-soluble oxide for analysis.

Referring to FIG. 1, a flow diagram illustrating an exemplary method of separating a metal from its water-soluble oxide 10 for analysis, the method steps of the present disclosure include: weighing a sample in digestion vials (not shown); dissolving 12 the metal oxide out of the sample into water for a specific period of time, (e.g., about 1 hour for borate), and at a specific temperature, (e.g., about 70° C. for borate); filtering 14 the sample into a filtrate 22 and a residue 16 where the filtrate contains borate, potassium, and nitrate ions, to a predetermined volume with an appropriate diluent, (e.g., about 2% by mass nitric acid ($HNO_3$) to 25 mL 24), where the filtering step separates the water soluble oxide 22, (e.g., borate), from the elemental fuel, (e.g., boron) which is the residue 16; digesting 18 the residue by means of an appropriate digestant, (e.g., about 5 mL of concentrated $HNO_3$), for a predetermined time, (e.g., about 1 hour), and at another predetermined temperature, (e.g., about 98° C.); bringing the digested residue to a known volume 20, (e.g., 50 mL), with, in this example, the same type of diluent substance as the filtrate.

Figure 2:
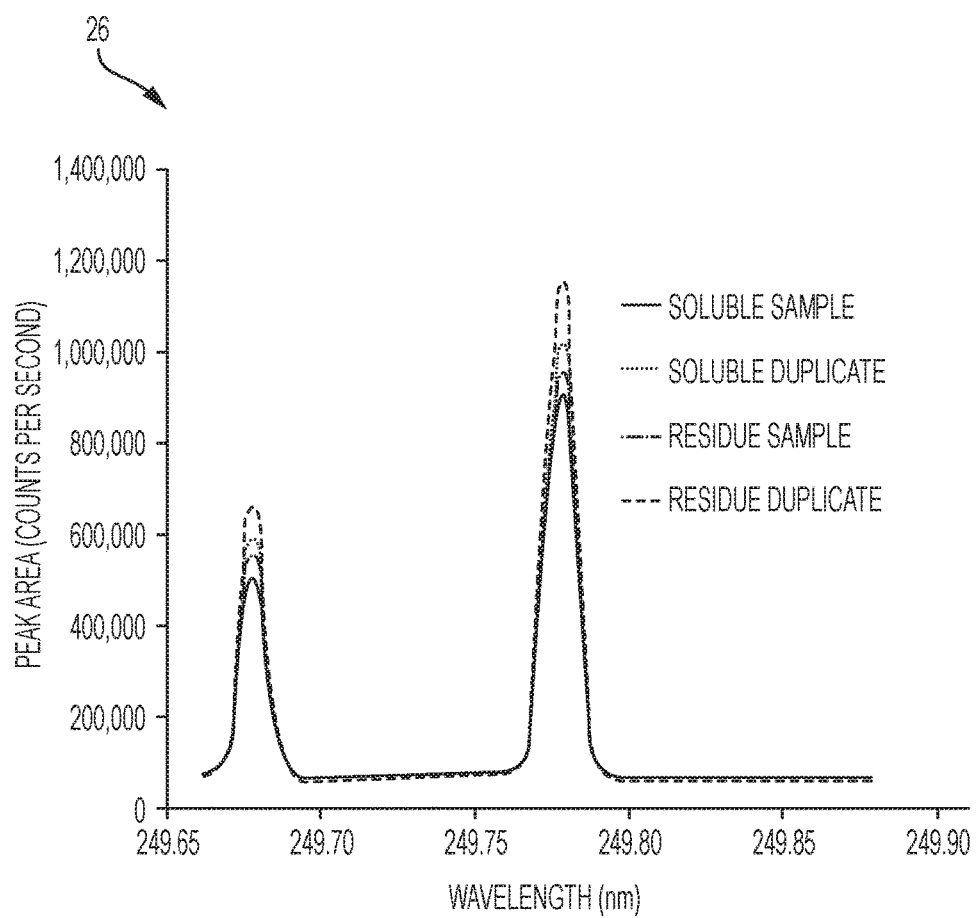
FIG. 2 shows a representative spectra for an exemplar 208.9 nanometers (nm) wavelength of boron.
Figure 3:
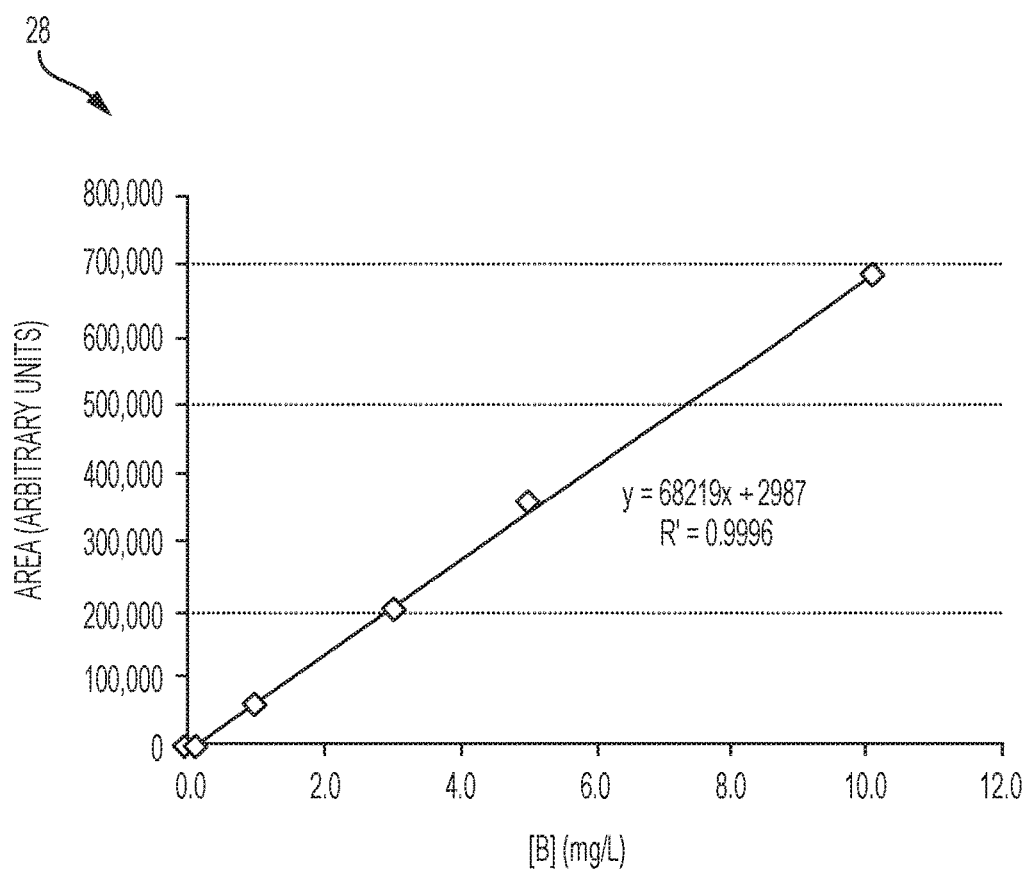
FIG. 3 shows a calibration curve used for an exemplar 249.8 nm line of boron testing using ICP-OES.

Referring to FIGS. 2-3, showing the representative spectra 26 for the 208.9 nm wavelength of boron and the calibration curve 28 used for the 249.8 nm line of boron on an analytical technique used for the detection of trace metals, (e.g., ICP-OES), the exemplary method further involves: conducting elemental analysis of the filtrate and digested elemental residue using a desired technique, (e.g., ICP-OES).

Referring to FIGS. 4-5, showing exemplary results for boron measurements for both exemplary residue portion 30 and the soluble portion 32, respectively. An exemplary method can also include computing a weight percent of both the elemental metal and the water-soluble oxide of that metal using initial mass, measured concentration of the element in both samples, and volume of each sample.

References herein to "about" can mean within twenty percent (20%) of a stated exemplar value.

Although the invention has been described in detail with reference to certain preferred embodiments, variations and modifications exist within the spirit and scope of the invention as described and defined in the following claims.

What is claimed is:

1. A method for separating a metal from its liquid-soluble metal oxide for analysis comprising:
    weighing a sample comprising at least one metal and a liquid-soluble metal oxide in a first container;
    dissolving said metal oxide out of said sample into a liquid for a first predetermined period of time, and at a first predetermined temperature;
    filtering said sample, thereby separating a filtrate comprising liquid soluble components of the sample from an elemental metal residue;
    transferring said filtrate into a second container;
    transferring said elemental metal residue into said first container or a third container;
    adding a diluent to said second container to bring said diluent and said filtrate to a first predetermined volume within said second container to produce a first solution;
    digesting said elemental metal residue in said first container or said third container by adding a digestant into said first container or said third container that reacts with said elemental metal residue to dissolve said elemental metal residue into said digestant for a second predetermined time and at a second predetermined temperature to produce a second solution comprising digested elemental metal residue and said digestant; and
    adding additional said diluent to said first container or said third container bringing said solution to a second predetermined volume with additional diluent to produce a second solution.

2. A method as in claim 1 further comprising conducting elemental analysis of contents of said first solution and said second solutions using an elemental analysis technique to determine at least one concentration of metal elements in each of said first solution and said second solutions.

3. A method as in claim 2, wherein said elemental analysis technique comprises inductively coupled plasma optical emission spectrometry (ICP-OES).

4. A method as in claim 1 further comprising computing a weight percent of both said metal and said water-soluble metal oxide of that metal using an initial mass value, a measured concentration of said metal in both samples, and a volume of each sample.

5. A method as in claim 1, wherein the filtering step separates said filtrate into a water soluble metal oxide from said metal and wherein said metal is said elemental metal residue.

6. A method as in claim 1, wherein said liquid comprises water.

7. A method as in claim 1, wherein said digestant comprises concentrated $HNO_3$ or nitric acid.

8. A method as in claim 1, wherein said diluent is about 2% by mass nitric acid ($HNO_3$).

9. A method as in claim 1, wherein said first predetermined period of time is about one hour for borate.

10. A method as in claim 1, wherein said first predetermined temperature is about 70° C. for dissolving borate and said second predetermined temperature is about 98° C. for digesting boron.

11. A method as in claim 1, wherein said at least one metal is boron and said liquid-soluble metal oxide is borate.

12. A method as in claim 1, wherein said filtrate comprises borate, potassium, and nitrate ions.

\* \* \* \* \*